US00PP20410P2

(12) United States Plant Patent
Renault

(10) Patent No.: US PP20,410 P2
(45) Date of Patent: Oct. 13, 2009

(54) ***CISTUS* PLANT NAMED 'RENCIS'**

(50) Latin Name: *Cistus×corbariensis*
Varietal Denomination: Rencis

(76) Inventor: Jean Renault, Le Brin d'Eau, 53120 Gorron (FR)

( * ) Notice: Subject to any disclaimer, the term of this patent is extended or adjusted under 35 U.S.C. 154(b) by 0 days.

(21) Appl. No.: 12/228,021

(22) Filed: Aug. 8, 2008

(51) Int. Cl.
*A01H 5/00* (2006.01)

(52) U.S. Cl. ..... Plt./226

(58) Field of Classification Search ..... Plt./226, Plt./263.1
See application file for complete search history.

*Primary Examiner*—David H Kruse
*Assistant Examiner*—June Hwu
(74) *Attorney, Agent, or Firm*—Penny J. Aguirre

(57) ABSTRACT

A new cultivar of *Cistus*, 'Rencis', characterized by its variegated leaves that are retained throughout the year with leaves with dark grey-green centers surrounded by yellow to creamy white colored margins that may become tinted with orange in autumn, its compact plant habit, and its white flowers present in late spring to early May.

2 Drawing Sheets

Botanical classification: *Cistus×corbariensis*.
Variety denomination: 'Rencis'.

BACKGROUND OF THE INVENTION

The present invention relates to a new and distinct cultivar of *Cistus×corbariensis* and will be referred to hereafter by its cultivar name, 'Rencis'. 'Rencis' is a new cultivar of evergreen shrub grown for use as a landscape plant.

The Inventor discovered 'Rencis' in his nursery in Gorron, France in July 1993. The new cultivar arose as a naturally occurring branch mutation of an unnamed plant of *Cistus×corbariensis* that was growing outdoors in a container in his nursery.

Asexual reproduction of the new cultivar was first accomplished by the Inventor using softwood stem cuttings in 1995 in Gorron, France. The cuttings were grown for a period of seven years in the Inventor's garden to test for stability prior to subsequent propagation. The characteristics of 'Rencis' have been determined to be stable and are reproduced true to type in successive generations.

SUMMARY OF THE INVENTION

The following traits have been repeatedly observed and represent the characteristics of the new cultivar as grown outdoors in a test garden in Gorron, France. These attributes in combination distinguish 'Rencis' as a unique cultivar of *Cistus*.

1. 'Rencis' exhibits variegated foliage with leaves having dark grey-green centers surrounded by yellow to creamy white colored margins. The margins become tinted with orange in autumn.
2. 'Rencis' exhibits foliage that is variegated throughout the year.
3. 'Rencis' exhibits a compact plant habit.
4. 'Rencis' exhibits white flowers in late spring to early summer.

'Rencis' differs from its parent plant, *Cistus×corbariensis*, in having variegated foliage, a more compact habit, and in producing less flowers. 'Rencis' can be compared to a cultivar of *Cistus* known by the Inventor to have variegated foliage; *Cistus* 'Candy Stripe' (unpatented). It is similar to 'Rencis' in having compact habit and foliage with yellow to gold margin, however, it differs from 'Rencis' in having margins narrow.

BRIEF DESCRIPTION OF THE DRAWING

The accompanying colored photographs illustrate the overall appearance and distinct characteristics of a 3 year-old plant of the new *Cistus* as grown outdoors in a 21 cm container in Gorron, France.

The photograph in FIG. 1 illustrates the overall appearance of 'Rencis'.

Figure 1:
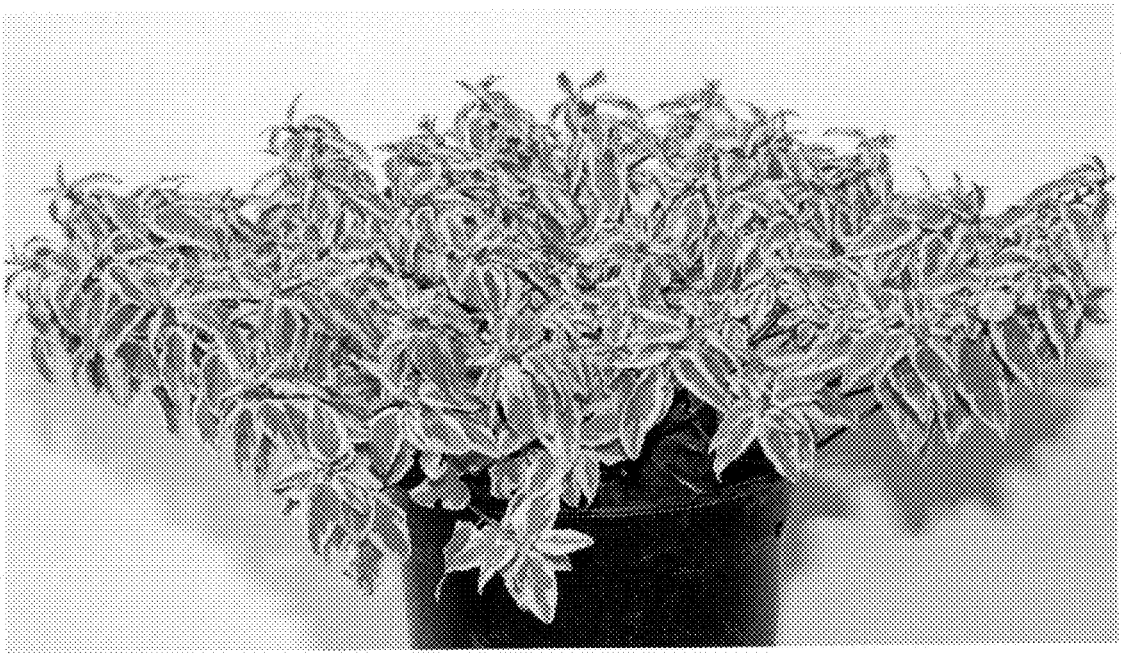
Figure 2:
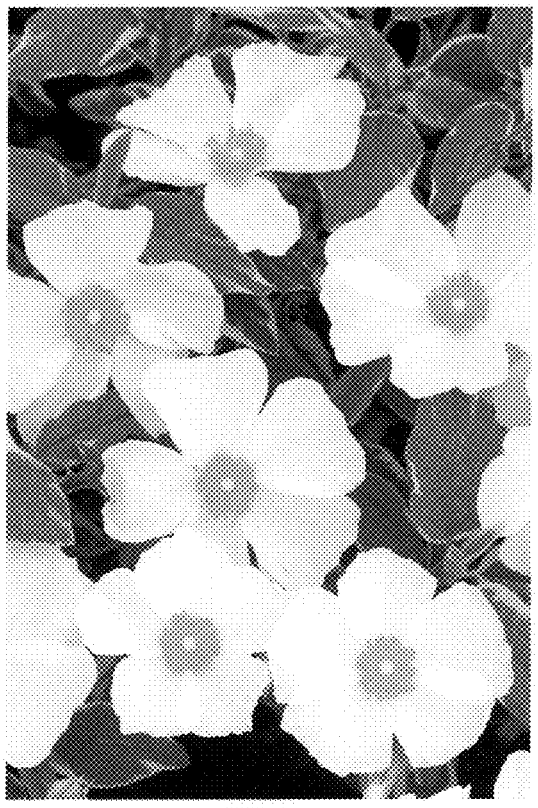

The photograph in FIG. 2 is a close-up view of the flowers

Figure 3:
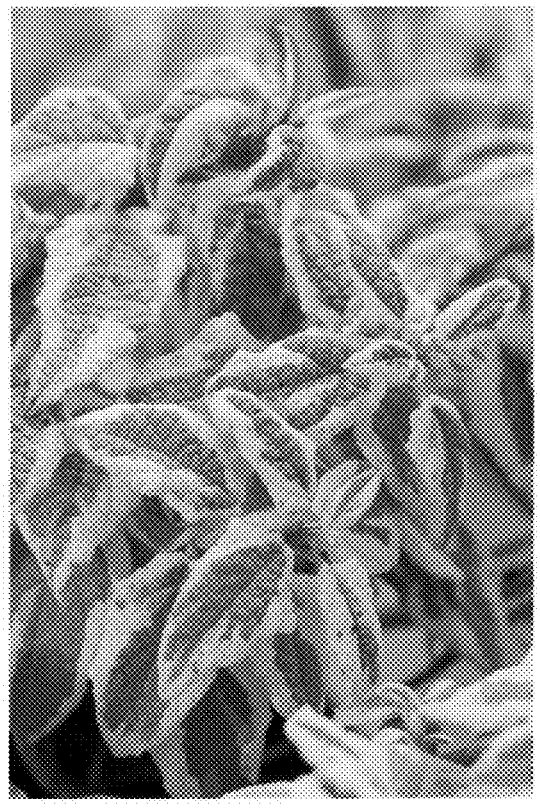

The photograph in FIG. 3 is a close-up view of the foliage of 'Rencis'.

The colors in the photographs are as close as possible with the digital photography techniques available, the color values cited in the detailed botanical description accurately describe the colors of the new *Cistus*.

DETAILED BOTANICAL DESCRIPTION

The following is a detailed description of 3 year-old plants of the new cultivar as grown outdoors in 21 cm containers in Gorron, France. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—Blooms for about 4 weeks in May to June in Gorron, France.

*Plant habit.*—Compact shrub, evergreen shrub, spreading to broadly upright.

*Height and spread.*—Reaches about 1.5 m in height and 1.2 m in width.

*Cold hardiness.*—At least in U.S.D.A. Zone 8a.

*Heat tolerance.*—At least to temperatures up to 35° C.

*Diseases resistance.*—No particular disease problems or resistance has been observed.

*Root description.*—Fibrous.

Growth and propagation:

*Propagation.*—Softwood stem cuttings.

*Root development.*—Roots develop in about 80 days in June under greenhouse conditions at 20° C.

*Root development.*—Crop finishes in about 12 months in a 13 cm container.

*Growth rate.*—Moderate.

Stem description:

*Shape.*—Round.

*Stem color.*—144C with upper surface tinged with 176A to 176B.

*Stem size.*—Lateral branches average 17.8 cm in length and 2 mm in width.

*Stem surface.*—Moderately glossy.

*Internode length.*—Average of 1.7 cm.

*Branching.*—Average of 52 lateral branches per 21 cm container.

Foliage description:

*Leaf shape.*—Ovate.

*Leaf division.*—Simple.

*Leaf base.*—Truncate.

*Leaf apex.*—Acute.

*Leaf fragrance.*—None.

*Leaf venation.*—Pinnate, color matched leaf color on upper surface and 143B in color on lower surface.

*Leaf margins.*—Denticulate and wavy.

*Leaf arrangement.*—Opposite.

*Leaf attachment.*—Petiolate.

*Leaf surface.*—Rugose, upper and lower surface moderately covered with stellate hairs about 0.2 mm in length and 162C to 162D in color.

*Leaf size.*—Average of 4.4 cm in length and 2.4 cm in width.

*Leaf quantity.*—Average of 18 on a branch 17 cm in length.

*Leaf variegation pattern.*—Dark grey-green centers surrounded by a yellow to creamy white colored margins, centers comprise about one third of the leaf area.

*Leaf color.*—Young leaves upper surface; centers 137A and margins 151B to 3A, young leaves lower surface; centers 137B to 137C and margins 5B, mature leaves upper surface; centers 137C and margins 10A, mature leaves lower surface; centers 138B and margins 8A to 8B, margins in fall become tinged with 22A.

*Petioles.*—An average of 8 mm in length and 1 mm in width, 144A to 144B in color.

*Stipules.*—None present.

Inflorescence description:

*Inflorescence type.*—Solitary at axillary nodes, occasionally in pairs.

*Flower buds.*—Ovate in shape, 150B to 150C in color with base 145A to 145B, about 9 mm in length and 5 mm in width, surface is glabrous.

*Flower fragrance.*—Very faint.

*Lastingness of flower.*—One day, self cleaning.

*Flower quantity.*—Average of 250 per plant in 21 cm container.

*Flower type.*—Rotate, single, slightly cup-shaped.

*Flower size.*—Average of 3.8 cm in diameter and 9 mm in depth.

*Peduncles.*—About 3.6 cm in length and 1 mm in diameter, 143C in color. glabrous surface, round in shape, held at an angle of about 30° to lateral branch.

*Pedicels.*—Present when flowers are produced in pairs, average of 9 mm in length and 0.8 mm in diameter, 143B in color, glabrous surface, round in shape, held at an angle of about 15° to peduncle.

*Calyx.*—Rotate in form, about 4 mm in depth and 1.3 cm in diameter.

*Sepals.*—5, broadly ovate in shape, apiculate apex, cordate base, smooth and moderately glossy surface, entire margin, average of 7 mm in length and 5 mm in width, color of upper and lower surface immature; 150B to 150C with base 145A to 145B, color of upper and lower surface mature; 145B with broad darker central band 144A to 144B.

*Petals.*—5, flabellate in shape, margin entire, cuneate base, praemorse to retuse apex, about 1.5 cm in length and 2 mm in width, surface is smooth and slightly crinkled, color when opening and mature on upper and lower surface is whiter than 155A with small basal spot 7A.

Reproductive organs:

*Gynoecium.*—Pistils; average of 10, average 0.2 mm in length, styles; about 0.1 mm in length and 155B in color, stigmas; crested, about 0.1 mm in diameter and 155B in color, ovaries; 145D in color.

*Androcoecium.*—Stamens; average of 100, filaments; about 4 mm in length and 13B in color, anthers; average of 0.8 mm in length and 14A in color, dorsifixed, narrow oblong in shape, pollen; moderate in quantity, 14A to 14B in color.

*Fruit and seed.*—No fruit or seed production has been observed.

It is claimed:

1. A new and distinct cultivar of *Cistus* plant named 'Rencis' as herein illustrated and described.

* * * * *